US008852917B2

(12) United States Patent
Hill et al.

(10) Patent No.: US 8,852,917 B2
(45) Date of Patent: Oct. 7, 2014

(54) **THURICIN CD, AN ANTIMICROBIAL FOR SPECIFICALLY TARGETING *CLOSTRIDIUM DIFFICILE***

(75) Inventors: Colin Hill, Cork (IE); Mary Rea, Fermoy (IE); Paul Ross, Kilworth (IE)

(73) Assignees: University College Cork, Cork (IE); TEAGASC, The Agriculture and Food Development Authority, Carlow (IE)

( * ) Notice: Subject to any disclaimer, the term of this patent is extended or adjusted under 35 U.S.C. 154(b) by 978 days.

(21) Appl. No.: 12/745,299

(22) PCT Filed: Nov. 28, 2008

(86) PCT No.: PCT/EP2008/066450

§ 371 (c)(1),
(2), (4) Date: Oct. 19, 2010

(87) PCT Pub. No.: WO2009/068656

PCT Pub. Date: Jun. 4, 2009

(65) Prior Publication Data

US 2011/0059060 A1 Mar. 10, 2011

(30) Foreign Application Priority Data

Nov. 30, 2007 (IE) .................................... 2007/0873

(51) Int. Cl.

| | |
|---|---|
| ***C12N 1/00*** | (2006.01) |
| ***C12N 1/12*** | (2006.01) |
| ***C12N 1/20*** | (2006.01) |
| ***C12N 11/00*** | (2006.01) |
| ***C12N 11/16*** | (2006.01) |
| ***C12P 1/00*** | (2006.01) |
| ***C12P 21/04*** | (2006.01) |
| ***C07K 14/32*** | (2006.01) |
| ***C12N 1/06*** | (2006.01) |
| ***C12R 1/07*** | (2006.01) |
| *A61K 38/00* | (2006.01) |
| *A61K 35/00* | (2006.01) |

(52) U.S. Cl.

CPC . *C07K 14/32* (2013.01); *C12N 1/06* (2013.01); *A61K 38/00* (2013.01); *C12R 1/075* (2013.01); *A61K 2035/11* (2013.01); *Y10S 435/832* (2013.01)

USPC ......... 435/252.5; 435/41; 435/71.1; 435/174; 435/252.1; 435/832

(58) Field of Classification Search

CPC ........... A61K 2300/00; A61K 31/7052; A61K 2039/53; A61K 39/092; A61K 2039/525; A61K 2039/555; A61K 31/198; A61K 31/522; A61K 31/7076; A61K 2039/60; A61K 2039/6031; A61K 39/155; A61K 39/165; A61K 39/21; A61K 48/00; A61K 45/06

See application file for complete search history.

(56) References Cited

FOREIGN PATENT DOCUMENTS

WO WO 99/66949 * 12/1999

* cited by examiner

*Primary Examiner* — Debbie K Ware
(74) *Attorney, Agent, or Firm* — Jackson Walker L.L.P.

(57) ABSTRACT

The present invention relates to a new bacteriocin, to microbial strains which can produce it and to uses of the bacteriocin and the strains. The bacteriocin is effective against *Clostridium difficile* and *Listeria monocytogenes* amongst other organisms.

15 Claims, 7 Drawing Sheets

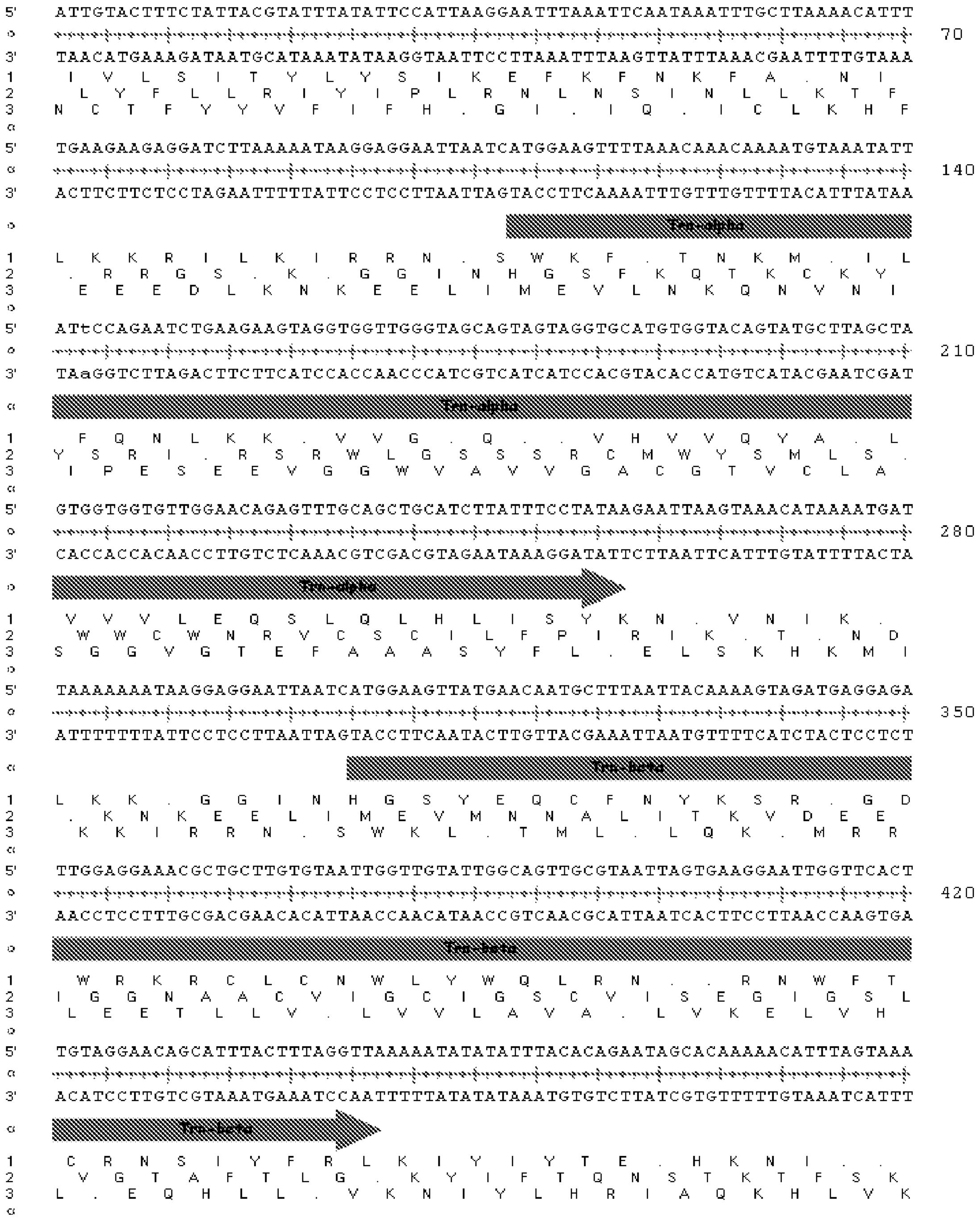

Figure 3.

```
5'   ATTGTACTTTCTATTACGTATTTATATTCCATTAAGGAATTTAAATTCAATAAATTTGCTTAAAACATTT
                                                                                       70
3'   TAACATGAAAGATAATGCATAAATATAAGGTAATTCCTTAAATTTAAGTTATTTAAACGAATTTTGTAAA
1      I  V  L  S  I  T  Y  L  Y  S  I  K  E  F  K  F  N  K  F  A  .  N  I
2       L  Y  F  L  L  R  I  Y  I  P  L  R  N  L  N  S  I  N  L  L  K  T  F
3     N  C  T  F  Y  Y  V  F  I  F  H  .  G  I  .  I  Q  .  I  C  L  K  H  F

5'   TGAAGAAGAGGATCTTAAAAATAAGGAGGAATTAATCATGGAAGTTTTAAACAAACAAAATGTAAATATT
                                                                                      140
3'   ACTTCTTCTCCTAGAATTTTTATTCCTCCTTAATTAGTACCTTCAAAATTTGTTTGTTTTACATTTATAA

1      L  K  K  R  I  L  K  I  R  R  N  .  S  W  K  F  .  T  N  K  M  .  I  L
2       .  R  R  G  S  .  K  .  G  G  I  N  H  G  S  F  K  Q  T  K  C  K  Y
3     E  E  E  D  L  K  N  K  E  E  L  I  M  E  V  L  N  K  Q  N  V  N  I

5'   ATtCCAGAATCTGAAGAAGTAGGTGGTTGGGTAGCAGTAGTAGGTGCATGTGGTACAGTATGCTTAGCTA
                                                                                      210
3'   TAaGGTCTTAGACTTCTTCATCCACCAACCCATCGTCATCATCCACGTACACCATGTCATACGAATCGAT

1      F  Q  N  L  K  K  .  V  V  G  .  Q  .  .  V  H  V  V  Q  Y  A  .  L
2       Y  S  R  I  .  R  S  R  W  L  G  S  S  S  R  C  M  W  Y  S  M  L  S  .
3     I  P  E  S  E  E  V  G  G  W  V  A  V  V  G  A  C  G  T  V  C  L  A

5'   GTGGTGGTGTTGGAACAGAGTTTGCAGCTGCATCTTATTTCCTATAAGAATTAAGTAAACATAAAATGAT
                                                                                      280
3'   CACCACCACAACCTTGTCTCAAACGTCGACGTAGAATAAAGGATATTCTTAATTCATTTGTATTTTACTA

1      V  V  V  V  L  E  Q  S  L  Q  L  H  L  I  S  Y  K  N  .  V  N  I  K  .
2       W  W  C  W  N  R  V  C  S  C  I  L  F  P  I  R  I  K  .  T  .  N  D
3     S  G  G  V  G  T  E  F  A  A  A  S  Y  F  L  .  E  L  S  K  H  K  M  I

5'   TAAAAAAATAAGGAGGAATTAATCATGGAAGTTATGAACAATGCTTTAATTACAAAAGTAGATGAGGAGA
                                                                                      350
3'   ATTTTTTTATTCCTCCTTAATTAGTACCTTCAATACTTGTTACGAAATTAATGTTTTCATCTACTCCTCT

1      L  K  K  .  G  G  I  N  H  G  S  Y  E  Q  C  F  N  Y  K  S  R  .  G  D
2       .  K  N  K  E  E  L  I  M  E  V  M  N  N  A  L  I  T  K  V  D  E  E
3     K  K  I  R  R  N  .  S  W  K  L  .  T  M  L  .  L  Q  K  .  M  R  R

5'   TTGGAGGAAACGCTGCTTGTGTAATTGGTTGTATTGGCAGTTGCGTAATTAGTGAAGGAATTGGTTCACT
                                                                                      420
3'   AACCTCCTTTGCGACGAACACATTAACCAACATAACCGTCAACGCATTAATCACTTCCTTAACCAAGTGA

1      W  R  K  R  C  L  C  N  W  L  Y  W  Q  L  R  N  .  .  R  N  W  F  T
2       I  G  G  N  A  A  C  V  I  G  C  I  G  S  C  V  I  S  E  G  I  G  S  L
3     L  E  E  T  L  L  V  .  L  V  V  L  A  V  A  .  L  V  K  E  L  V  H

5'   TGTAGGAACAGCATTTACTTTAGGTTAAAAATATATATTTACACAGAATAGCACAAAAACATTTAGTAAA
3'   ACATCCTTGTCGTAAATGAAATCCAATTTTTATATATAAATGTGTCTTATCGTGTTTTTGTAAATCATTT

```

A
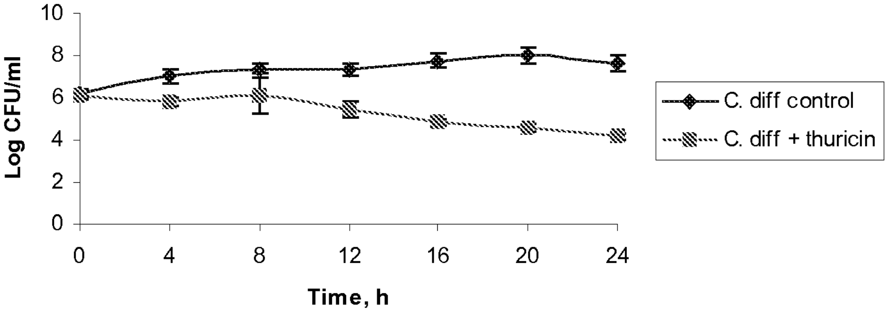
B
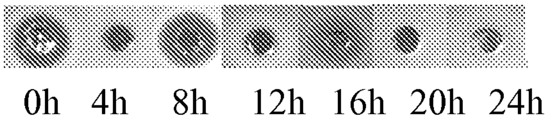
C
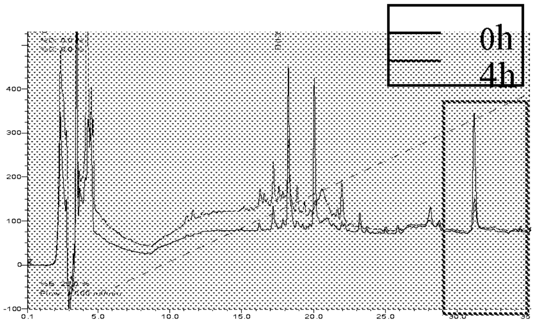
Figure 6.

A

B

C

D

E

THURICIN CD, AN ANTIMICROBIAL FOR SPECIFICALLY TARGETING *CLOSTRIDIUM DIFFICILE*

This application is a 371 of PCT/EP08/66450, filed Nov. 28, 2008.

FIELD OF THE INVENTION

The present invention relates to a microbial strain, which produces a bacteriocin having a narrow spectrum of inhibition but being effective, particularly against *C. difficile* and *Listeria monocytogenes* and to the bacteriocin produced by the strain.

BACKGROUND TO THE INVENTION

With the upsurge in antibiotic resistance among pathogens and the increase in hospital acquired infections such as MRSA and *C. difficile* there is a renewed urgency in discovering novel antimicrobial compounds to combat these diseases. First described in 1935, *C. difficile* was not recognised as the causative agent of nosocomial diarrhoea until the 1970s (George et al., 1978; Hall & O'Toole, 1935). However, *Clostridium difficile* associated disease (CDAD) is the now most common hospital acquired diarrhoea and is a major problem of gastroenteritis infection and antibiotic associated diarrhoea in nursing homes and care facilities for the elderly. Indeed, the health protection agency in UK reported 32,189 cases of CDAD for the first 6 months of 2007 in UK. The main predisposing factor for the acquisition of CDAD is antibiotic therapy. In the 1970s the administration of clindamycin followed by ampicillin and amoxicillin were implicated as the inducing agents of CDAD; these were replaced by cephalosporins in the 1980s and more recently by flouroquinolones (Aronsson et al., 1985; Bartlett, 2006; Winstrom et al., 2001). There is also the added problem of the hyper-virulent strain of *C. difficile* PCR ribotype 027, the incidence of which is increasing in US, Canada and Europe (Bartlett, 2006). Antimicrobial peptides produced by bacteria, now designated as bacteriocins, first came to prominence ~80 years ago with the discovery by Rogers & Whittier (1928) of nisin by *Lactococcus lactis* subsp. *lactis* which demonstrated a broad spectrum of activity against other lactic acid bacteria (LAB) and other Gram positive organisms. While the bacteriocins produced by LAB are the most widely studied and tend in the main to have a broad spectrum of activity, antimicrobial compounds are produced by many other bacterial species including Gram positive organisms *Bacillus* (Ahern et al., 2003; Bizani et al., 2005; Cherif et al., 2003; Cherif et al., 2001; Seibi et al. 2007, Teo & Tan, 2005); *Clostridium* (Kemperman et al., 2003), Gram negative organisms *E. coli* (Trautner et al., 2005), *Shigella* (Padilla et al., 2006).

Work carried out previously on various strains of *B. thuringiensis* have yielded a variety of bacteriocins (Ahern et al. 2003, Chehimi et al. 2007, Cherif et al. 2001, Favret and Yousten 1989, Gray et al. 2006a, Gray et al. 2006b,) demonstrating bactericidal properties against *B. thuringiensis* strains, *B. cereus* strains, and *Listeria monocytogenes* strains. However, these bacteriocins do not exhibit two-component activity.

Previous work by Yudina et al. describes proteins of parasporal crystals (Cry proteins) from entomopathogenic bacterium *B. thuringiensis* (subsp. *Kurstaki, galleriae, tenebriois*) as well as some fragments thereof, obtained by limited proteolysis which are capable of antimicrobial action against anaerobic bacteria and *C. butyricum, C. acetobutylicum* and *Methanosarcina barkeri*. U.S. Pat. No. 7,247,299 describes antimicrobial heat-stable compounds isolated from a novel strain of *B. subtilis* (deposited 8.5.05) isolated from the GIT of poultry, which are effective against *C. perfringens, C. difficile, Campylobacter jejuni, Camp. coli*, and *S. pneumoniae*. U.S. Pat. No. 7,144,858 describes the synthesis of new antibiotic compounds for use against Gram positive bacteria such as *Bacillus* (including *B. thuringiensis*), *Clostridium* (including *C. difficile*), *Streptococcus, Mycobacterium*, and *Staphylococcus*. US Application 20080213430 describes the artificial synthesis and recombinant expression of antibacterial peptides against bacteria such as *B. subtilis, C. difficile, E. coli, Staphylococcus*, and the like. However, these peptides have a broad spectrum of inhibition against a wide range of Gram positive organisms. Previous work using the naturally occurring lantibiotics lacticin and nisin have shown that these microbially derived peptides are effective in killing *C. difficile* at concentrations that compare well with commonly used antibiotics such as vancomycin and metronidazole (Bartoloni et al., 2004; Rea et al., 2007).

However, these lantibiotics have a broad spectrum of inhibition against a wide range of Gram positive organisms including those which would be considered beneficial to human gut health such as *Lactobacillus* and *Bifidobacterium*. Indeed, previous work in this laboratory has demonstrated that lacticin 3147 negatively affects the levels of *Lactobacillus* and *Bifidobacterium* in faecal fermentation (Rea et al., 2007). The aim of this study was therefore to isolate bacteria which produce narrow spectrum antimicrobial compounds which target *C. difficile*. To this end spore forming bacteria in the human gut were targeted; this would not be an obvious source of antimicrobials against *C. difficile.*

OBJECT OF THE INVENTION

The object of the invention is to provide an agent effective against *L. monocytogenes* and *C. difficile* but not against organisms considered beneficial to human or animal health. A further object is to provide compositions comprising such an agent, which can be used as disinfectants or antiseptics, as probiotic components in foodstuffs or as pharmaceutical compositions.

SUMMARY OF THE INVENTION

According to the present invention there is provided a bacterial strain *Bacillus thuringiensis* 6431 as deposited with the National Collection of Industrial and Marine Bacteria under the Accession No. 41490 and strains which are substantially similar thereto, also encoding a bacteriocin effective against *Listeria monocytogenes* and *Clostridium difficile*, but not against *Bifidobacterium* and *Lactobacillus* species. The strain was deposited on 9 Jul. 2007.

Suitably the strain produces a bacteriocin which is not effective against Gram positive flora of the gastro-intestinal tract.

The invention also provides a bacteriocin effective against *Listeria monocytogenes* and *Clostridium difficile*, produced by this bacterial strain.

In a still further aspect the invention provides a bacteriocin designated Thuricin CD comprising 2 peptides, Trn-$\alpha$ and Trn-$\beta$, Trn-$\alpha$ having a molecular mass of about 2763 and Trn-$\beta$ having a molecular mass of about 2861. The bacteriocin is heat-stable up to about 85° Centigrade, with a reduction of activity at about 90° Centigrade and a loss of activity at about 100° Centigrade after 15 minutes' incubation. By heat-stable we mean that the bacteriocin is not readily subject to destruction or alteration by heat. Thuricin CD has the ability to inhibit *Clostridium difficile* and *Listeria monocytogenes*. Thuricin CD is active in the pH range 2-10.

Suitably, the bacteriocin is not effective against *Bifidobacterium* and *Lactobacillus* species. The bacteriocin may not be effective against Gram positive organisms found in the gastro-intestinal tract. Suitably the bacteriocin is also effective against *Bacillus cereus*, other *Bacillus thuringiensis* strains, *Clostridium perfringens, B. mycoides*, and *B. firmus, Clostridium difficile* ribotype 027, *C. tyrobutyricum, C. lithuseburense* and *C. indolis*. By not effective we mean that the bacteriocin does not affect the viability of these organisms.

The bacteriocin may have a bacteriocidal effect against *C. difficile* of approximately $5\times10^6$ CFU of *C. difficile* per ml. being killed within 60 minutes and 180 minutes when thuricin CD is present at a concentration of 5 μM and 200 AU/ml respectively.

The bacteriocin is effective at nanomolecular concentrations.

The bacteriocin has been shown not to effect the viability of the probiotic strains *Lactobacillus casei* 338 or *Bifidobacterium lactis* Bb12.

The bacteriocin may have an inhibition spectrum as shown in Table 2.

Preferably the bacteriocin is one in which the component thuricin Trn-α has an N-terminal amino acid sequence GNAACVIGCIGSCVISEGIGSLVGTAFTLG and thuricin CD component Trn-β has the N-terminal amino acid sequence GWVAVVGACGTVCLASGGVGTEFAAASYFL. Preferably, the bacteriocin is one in which the Trn-α and Trn-β components have the amino-acid sequences as shown in FIG. 3, with or without the leader peptide sequence, or sequences which are substantially similar thereto and which also exhibit bacteriocin activity.

In a still further aspect the invention provides a host cell comprising the Thuricin CD component Trn-α encoding gene or the Trn-β encoding gene. The host cell may also comprise the thuricin CD component Trn-α and Trn-β-encoding gene. Preferably, the genes have the nucleic acid sequences as shown in FIG. 3, or sequences which are substantially similar thereto and which also encode bacteriocin activity.

By "substantially similar" is meant sequences which because of degeneracy of the genetic code, substitution of one amino-acid for another, or changes in regions of the amino-acid sequence which are not critical to bacteriocin activity, still result in a bacteriocin molecule having the properties defined herein.

The invention also provides Thuricin CD component Trn-α, and Thuricin CD component Trn-β.

Also provided is a disinfectant composition comprising the bacterial strain, a host cell, a bacteriocin or a Thuricin CD component Trn-α or Trn-β as defined above.

The invention provides a probiotic culture comprising vegetative cells or spores of a strain or a host cell as defined above. The strain or cell may be inactivated so that the strain is no longer viable.

Also provided is a sporicidal composition comprising the bacterial strain, a host cell, a bacteriocin or a Thuricin CD component Trn-α or Trn-β as defined above.

Also provided is a pharmaceutical composition comprising the bacterial strain, a host cell, a bacteriocin or a Thuricin CD component Trn-α or Trn-β as defined above, together with pharmaceutically effective carriers or excipeients. The pharmaceutical composition may be formulated as an enema preparation, as an encapsulated peptide with targeted delivery to the colon, as an encapsulated probiotic for targeted delivery to the colon, as an animal or veterinary preparation for use or as a probiotic or purified peptide.

The Trn-α and/or Trn-β peptide may be used without the presence of a live organism as food ingredient for control of *L. monocytogenes* in food. The invention also finds use in the control of *C. perfringens* in poultry.

The disinfectant, pharmaceutical, sporicidal, food, or other compositions may be formulated together with appropriate carriers or excipients.

BRIEF DESCRIPTION OF THE DRAWINGS

FIG. 3 The orientation of the genes encoding the thuricin peptides Trn-α and Trn-β.

FIG. 6 The effect of 500 μg/ml thuricin CD on the growth of *C. difficile* ribotype 001 in a model faecal fermentation when added at 0, 8 and 16 h (A). Activity of thuricin CD during the course of the fermenatation (B). Detection by RP-HPLC of thuricin peptides Trn-α and Trn-β at 0 h (black line) and after 4 h fermentation in the model faecal environment (C).

DETAILED DESCRIPTION OF THE INVENTION

Bacterial Strains Used

Figure 1:
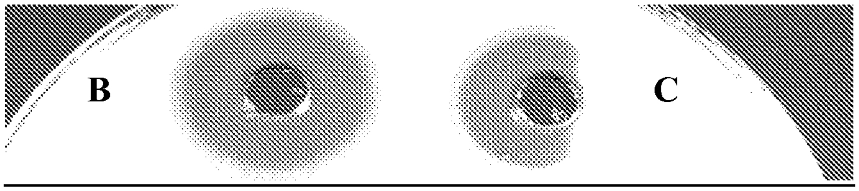
FIG. 1: Inhibition of *C. difficile* ATCC 43593 by cell free supernatant of *B. thuringiensis* DPC 6431(A), and demonstration of its proteinaceous nature through the effect of Proteinase K (B).

*C. difficile* ATCC 42639 was used as target strain for Well Diffusion Assays (WDA). *C. difficile* R027 NAP1 was used for bacteriocin sensitivities in time kill studies. A full list of target organisms and their sources which were used for determination of the spectrum of inhibition of the bacteriocin producing cultures is outlined, together with the media and growth conditions in Table 1. *B. cereus* NCIMB 700577 and *B. thuringiensis* NCIMB 701157 were used as positive controls for the PCR reaction using gyrB primers.

Isolation of Bacteriocin Producing Cultures.

Faecal samples from both diseased and healthy individuals were received in the laboratory and frozen at −80° C. On the day of analysis samples were thawed at room temperature and mixed with equal volumes of ethanol, and allowed to stand at room temperature for ~30 min. Samples were subsequently serially diluted in anaerobic diluent, 100 μl spread on the surface of Wilkens Chargrin Anaerobic Agar (WCAA) and grown for 5 days at 37° C. in an anaerobic chamber. Colonies which developed were overlaid with ~10 ml of Reinforced *Clostridium* Agar (RCA) inoculated at 1.25% with a log phase culture of *Clostridium difficile* ATCC 43593. The plates were incubated for a further 18 h and inspected for zones of inhibition of the overlaid culture. Colonies showing a clear zone of inhibition were sub-cultured onto fresh WCAA having first removed the agar overlay using a sterile scalpel. Approximately 30,000 colonies were screened and one colony showing potent antimicrobial activity against the overlaid *C. difficile* strain was purified and stocked at −80° C. on Microbank Beads and designated as DPC6431 and the inhibitory substance produced was designated thuricin CD.

Genotypic Characterisation 16S rDNA Sequencing of DPC 6431

Genomic DNA was isolated from overnight broth cultures of *B. thuringiensis* DPC 6431 and amplified by PCR as described by (Simpson et al., 2003). Comparisons of the 16S rDNA sequences were obtained using the BLAST programme that allowed the assignment of a strain to a particular species.

Identification to Species Level Using gyrB Primers

Species-specific oligonucleotide primers for the gyrB gene for *B. cereus, B. thuringiensis* and *B. anthracis* were purchased from MWG with sequences as described by Yamada et al., (1999). PCR products were analysed on 1.5% agarose gel with 100 bp ladder as molecular marker and visualised using an AlphaImager 3400. *B. cereus* NCIMB 700577 and *B. thuringiensis* NCIMB 701157 were used as positive controls. Because of the pathogenic status of *B. anthracis* there was no positive control for *B. anthracis*.

Production of Thuricin CD from Cell Free Supernatants:

*B. thuringiensis* DPC 6431 was grown aerobically from stock for ~6 h in BHI broth and sub-cultured into fresh BHI at 0.1% for 18 h in BHI. Following growth, the culture was centrifuged twice at 8200 g for 10 min. Activity was determined using the well diffusion assay (WDA) as described by Ryan et al., (1996). Activity against a range of target organisms was determined by WDA. Cultures were grown overnight in various broth media and temperatures as outlined in Table 1. Twenty ml of the appropriate agar medium was inoculated with 100 μl of target organism and, once solidified, 50 μl of the cell free supernatant (CFS) of *B. thuringiensis* DPC 6431 was added to a well made in the agar. Plates were incubated under conditions appropriate for the various target organisms as outlined in Table 1. Zones of inhibition (mm) were measured and relative sensitivity determined by measuring the diameter of the zone. Zones of size ≤9 mm were designated +; of 10-15 mm were designated ++; of 16-21 mm were designated +++; of ≥22 mm were designated ++++;

Sensitivity of Thuricin CD to Enzymatic Degradation, Heat and pH.

The cell free supernatant was tested for sensitivity to the following enzymes at a concentration of 25 mg/ml: pepsin, trypsin, peptidase, α-chymotrypsin type V111, α-chymotrypsin type 11 and proteinase K. All enzymes were purchased from Sigma. Cell free supernatants were incubated with the enzymes for 1 h at 37° C. Activity post enzyme treatment was determined using the well diffusion method using *C. difficile* ATCC 43593 as the target organism. Sensitivity of the antimicrobial to Proteinase K was also determined by applying 5 μl of Proteinase K (6.5 mg/ml) to the edge of the well containing the sample.

Activity over a range of pH was determined in CFS by adjusting pH from 2 to 9 using either 0.5M HCl or 1M NaOH. The effect of acid or base on the target organism was determined using uninoculated broth medium adjusted through the pH range. Activity was determined using WDA assay using *C. difficile* ATCC 43593 as the target strain. Heat sensitivity was determined by heating the CFS for 15 min at a range of temperatures from 37° C. to 100° C.; the control was incubated at 37° C. Activity was determined using WDA with *C. difficile* ATCC 43593 as the target organism.

Determination of the Thuricin CD Production During Growth.

*B. thuringiensis* DPC 6431 was sub-cultured twice in BHI broth and then inoculated again at 1% into BHI broth; growth was followed by measuring absorbance at $600_{nm.}$ Samples, taken at intervals during growth for determination of antimicrobial production, were centrifuged twice at 8200 g for 10 min, serially diluted and 50 μl of each dilution inoculated into wells in agar plates seeded with *C. difficile* ATCC 43593. Activity units were determined by WDA.

Purification and Molecular Mass Determination of Thuricin CD.

Production of Thuricin CD:

Tryptone Yeast Broth (TYB) was made up as follows: Tryptone (Oxoid) 2.5 g; Yeast extract (Oxoid) 5.0 g; $MgSO_4 7H_2O$ 0.25 g; $MnSO_4 4H_2O$ 0.05 g were dissolved in 900 ml distilled $H_2O$. The media was clarified, before autoclaving at 121° C. for 15 minutes, by passing through a column containing propan-2-ol washed XAD beads (Sigma-Aldrich). Before use, filter sterilised glucose and β-glycerophosphate were added to give a final concentration of 10 g and 19 g/l respectively and a final volume of 1 l.

*Bacillus thuringiensis* DPC 6431 was sub-cultured twice in BHI broth at 37° C. before use. Two liters of TYB were inoculated with the culture at 0.1% and incubated shaking at 37° C. over-night. The culture was centrifuged at 8,280 g for 15 minutes. The cell pellet and supernatant were retained. The cells were resuspended in 200 ml of 70% propan-2-ol pH 2.0 per liter of broth and stirred at 4° C. for 4 h. The culture supernatant was passed through XAD beads, pre-washed with 1 l of distilled $H_2O$. The column was washed with 500 ml of 30% ethanol and the inhibitory activity eluted in 400 ml of 70% propan-2-ol pH 2.0 and retained ($S_1$). The cells that had been resuspended in 70% propan-2-ol pH 2.0 were centrifuged at 8,280 g for 15 minutes and the supernatant ($S_2$) retained; $S_1$ and $S_2$ were combined. The propan-2-ol was evaporated using a rotary evaporator (Buchi) and the sample applied to a 6 g (20 ml) Phenomenex C-18 column pre-equilibrated with methanol and water. The column was washed with 2 column volumes of 30% ethanol and the inhibitory activity was eluted in 1.5 column volumes of 70% propan-2-ol pH 2.0. This preparation was concentrated using rotary evaporation before separation of peptides using HPLC as follows: aliquots of approximately 2 ml were applied to a Phenomenex (Phenomenex, Cheshire, UK) $C_{18}$ reverse phase (RP)-HPLC column (Primesphere 10μ C18-MC 30, 250×10.0 mm, 10 μm) previously equilibrated with 45% acetonitrile, 0.1% trifluoroacetic acid TFA. The column was subsequently developed in a gradient of 45% acetonitrile containing 0.1% TFA to 65% acetonitrile containing 0.1% TFA from 4-40 minutes at a flow rate of 9.9 ml/min. Biologically active fractions were identified using *C. difficile* as target organism in WDA. Fractions containing the active peptides were pooled, freeze dried and reconstituted at the required concentration in 70% propan-2-ol pH 2.0 and frozen at −20° C. until use. Subsequent dilutions were made in sterile 50 mM phosphate buffer pH 6.5.

Molecular Mass Determination of Thuricin CD:

Mass spectrometry was performed on biologically active fractions with an Axima CFR plus MALDI TOF mass spectrometer (Shimadzu Biotech, Manchester, UK). A 0.5-μl aliquot of matrix solution (-cyano 4-hydroxy cinnamic acid, 10 mg/ml in acetonitrile-0.1% (v/v) trifluoroacetic acid) was deposited onto the target and left for 5 seconds before being removed. Any residual solution was allowed to air-dry and the sample solution deposited onto the pre-coated sample spot; 0.5 μl of matrix solution was added to the deposited sample and allowed air-dry. The sample was subsequently analysed in positive-ion reflectron mode to determine molecular mass.

Determination of Amino Acid Sequence of Biologically Active Peptides.

N-terminal amino acid determination of biologically active fractions was carried out by Edman degradation at Aberdeen Proteome Facility, University of Aberdeen, Aberdeen, Scotland, UK.

Determination of Nucleotide Sequence of Thuricin CD

Degenerate primers, based on the partial amino acid sequences of the 2 peptides, were designed with the following sequences: Trn-α-F/FC 5' GGT TGG GTA GCA GTA GTA GGT GCA TGT GGW ACA GTW ACC CAWCC; Trn-α-R/FC 5'CGT AAA CAT ACT GTA CCA CAT GCA CCT ACT ACW GCW ACC CAW CC;: Trn-β-F/FC 5' GGT AAT GCA TGT GTA WTW GGW TGT WTW GG; Trn-β-R/FC 5' CCA ATA CGA CCA ATT ACA CAW GCW GCW TTW CC. Chromosomal DNA was extracted from *B. thuringenisis* using the Qiagen QiAamp DNA Mini Kit. PCR was performed on extracted DNA using the following conditions: 94° C.×5 min; 94° C.×1 min, 64.5° C.×1 min, 72° C.×1 min 25 cycles with temperature gradient of 64.5° C.-69.5° C.; final extension step 72° C.×7 min. The Trn-α-F/FC/Trn-β-R/FC primer combination resulted in a PCR product of ~220 bp. This product was purified using Qiagen Qiaquick PCR purification Kit and cloned using the Invitrogen TOPO TA Cloning kit (A). The presence of the cloned fragment was confirmed by restriction analysis of recombinant plasmids with EcoR1 (NEB), used according to the manufacturer's instructions. Recombinant plasmid DNA was then sequenced commercially by Lark (Windmill Road Headington OX3 7BN Oxford, UK) using the T7 and T3 priming sites. Sequence assembly and analysis was performed using the SeqBuilder and Seqman programmes from the Lasergene software package. (DNASTAR, Madison, Wis.). The consensus sequence was further analysed by database searches using the Blastn, Blastp and tBlastx programmes.

Inverse PCR to Obtain the Surrounding DNA Regions

Inverse PCR primers, based on the DNA sequence of the fragment encoding the two peptides that was isolated by degenerate PCR (above) were designed with the following sequences: Primer FCin1: 5' CAT GCA CCT ACT GCT ACC CAA CC 3' and Primer FCin2: 5' CAG AGT TTG CAG CTG CAT CTT ATT TCC 3'.

Chromosomal DNA was extracted from *B. thuringenisis* using the Qiagen QiAamp DNA Mini Kit and digested with the restriction enzyme HindIII (NEB) according to manufacturer's instructions. Digested DNA was then relegated at concentrations known to encourage the formation of monomeric molecules. Inverse PCR was performed using Expand Long Template DNA polymerase (Roche) according to the manufacturer's instructions. This resulted in amplification of a product of ~4500 bp. This product was purified using Qiagen Qiaquick PCR purification Kit and cloned using the Invitrogen TOPO TA Cloning kit (A). The presence of the cloned fragment was confirmed by restriction analysis of recombinant plasmids with EcoR1 (NEB), used according to the manufacturer's instructions. Recombinant plasmid DNA was then sequenced commercially by Lark (Windmill Road Headington OX3 7BN Oxford, UK) using the T7 and T3 priming sites and primer walking. Sequence assembly and analysis was performed using the SeqBuilder and Seqman programmes from the Lasergene software package. (DNASTAR, Madison, Wis.). The consensus sequence was further analysed by database searches using the Blastn, Blastp and tBlastx programmes.

Specific Activity Determination.

Ninety-six well microtiter plates were used to determine the $MIC_{50}$ of thuricin CD. $MIC_{50}$ was defined as the concentration of peptides at which 50% inhibition of growth of *C. difficile* ATCC 43493 occurred. One hundred and fifty microliters of 3 replicate overnight cultures, diluted 1:10 in reinforced *clostridium* medium (RCM) which had been previously boiled and cooled, were inoculated into triplicate into wells of 96 well microtitre plates in an anaerobic chamber. Thuricin CD Trn-α and Trn-β were added to the wells at varying concentrations both singly and in combination and final volume made up to 200 μl with sterile 50 mM phosphate buffer. Control wells contained 150 μl culture and 50 μl buffer (positive control) or 150 μl uninoculated broth medium and 50 μl buffer (blank). The optical density at $600_{nm}$ was recorded after 5 h anaerobic incubation at 37° C. Triplicate readings were averaged and the $OD_{600\ nm}$ values for the uninoculated medium were subtracted from each value. A 50% growth inhibition was determined as half the final $OD_{600\ nm}$+/−0.05 of the control culture. The concentrations of Trn-α in combination with Trn-β which caused 50% inhibition were plotted to generate an isobologram. The specific activities and optimum ratios of the 2 peptides were determined at the point of intersection of the x- and y-axis.

Demonstration of Activity of Thuricin CD Using Kill Curves.

The effect of thuricin against *C. difficile* R027 NAP1, *L. monocytogenes* NCTC 5348, *Lb. casei* 338 and *B. lactis* Bb12 was determined in Reinforced *Clostridium* Medium (RCM Merck), Brain Heart Infusion broth (Merck), MRS (de Mann-Rogosa-Sharpe) medium (Difco) and MRS containing 0.05% cystein respectively. Three independent cultures were prepared for each strain and grown overnight at 37° C. Three replicate one ml volumes of sterile double strength broth medium was prepared for each strain and inoculated with the test organisms to give initial cell numbers of $10^5$-$10^6$/ml. Thuricin was added to give the required concentration and the volume made up to 2 ml with sterile distilled water. The bacteriocin was omitted from the control and volume substituted with sterile water. Samples were removed at intervals, serially diluted and plated on RCA, BHI agar, MRS agar or MRS agar containing 0.05% cystein depending on the strain. Plates were counted after 24 h (*L. monocytogenes*), or 48 h (*C. difficile, Lb. casei* 338 and *B. lactis* Bb12) incubation at 37° C.

Determination of Minimum Inhibitory Concentrations

*C. difficile* ribotypes 001, 106 and 027 were taken from −80° C. stock and grown on Fastidious Anaerobic Agar containing 7% defibrinated horse blood. Before use a colony was transferred into each of three 10 ml volumes of RCM and grown over-night at 37° C. The cultures were then sub-cultured into 10 ml fresh RCM at 1%. Three replicates were set up for each strain. Cultures were grown for 6 h anaerobically at 37° C. Solutions of vancomycin and metronidazole were prepared in water and solutions of thuricin diluted from the stock solution in 50 mM phosphate buffer pH 6.5. Triplicate serial two-fold dilutions of the antimicrobial compounds (100 μl) were prepared in microtitre plates for each compound. *C. difficile* strains were diluted 1:10 in double strength RCM and 100 μl was added to each well. Controls for each strain were set up without the addition of antimicrobials. The microtitre plates were incubated for 16 h at 37° C. anaerobically and the OD of the plates read after incubation using a microtitre plate reader. The MIC was defined as the concentration at which there was no evidence of growth.

Demonstration of Lysis of *C. difficile* by Thuricin CD.

The lytic effect of thuricin CD on *C. difficile* was carried out as described by Rea et at (2007).

Determination of Thuricin Stability in Faecal Fermentation

Preparation of *C. difficile* Inoculum:

*C. difficile* DPC 6537 (PCR Ribot e 001) was taken from −80° C. stock and streaked on Fastidious Anaerobic Agar and incubated anaerobically at 37° C. On the night before the experiment ~1 colony was inoculated into 10 ml of RCM which has been previously boiled and cooled and incubated anaerobically at 37° C.

Preparation of Faecal Medium:

Faecal growth medium was prepared as described by Fooks and Gibson (2003) with minor modifications as follows. The ingredients were made up to 800 ml, the pH adjusted to 6.8. One hundred and sixty ml was added to each fermentation vessel and autoclaved at 121° C. for 15 min. Prior to inoculation the faecal medium was sparged with $O_2$-free nitrogen for ~1 h. A 20% faecal slurry was made from a fresh faecal sample in 50 mM phosphate buffer containing 0.05% cystein which has been previously boiled and cooled just prior to use and mixed using a stomacher for no longer than 1 min. Two fermentor vessels were inoculated with 35 ml of the slurry preparation and 2 ml of the overnight culture of *C. difficile*. To the test vessel 1 ml of 100 mg/ml thuricin was added at 0, 8 and 16 h incubation and both vessels sampled at 0, 4, 8, 12, 16, 20 and 24 h for both microbiological analyses of *C. difficile* and *Bifidobacteria* sp. Samples were also taken for analysis of thuricin activity using WDA and MALDI-TOF MS.

Stability of Thuricin:

The stability of thuricin during fermentation was measured using WDA using RCM agar plates seeded with *C. difficile* as described previously. One ml samples were also centrifuged and passed through activated 1 ml $C_{18}$ SPE columns and the peptides eluted with 70% propan-2-01. The presence of individual peptides was measured using RP-HPLC as described previously in this document.

Microbiological Analyses:

*C. difficile* was enumerated on CCEY agar (LabM) and *Bifidobacterium* sp. on modified MRS agar containing 0.05% cystein and 50 mg mupirocin/1 after 48 h and 72 h at 37° C. incubation respectively.

These experiments were carried out in duplicate

Stability of Thuricin CD in Simulated and Porcine Gastric Juices

Effect of simulated gastric, ileal and colon juice on stability of thuricin CD *C. difficile* 64539 was grown overnight and inoculated at 1.25% into Reinforced *Clostridium* Agar (RCA). Simulated gastric, ileal and colon juice were prepared as outlined by Breumer et al (1992). Purified thuricin CD was made up to 100 mg/ml in 70% IPA. Seventy μl (1 mg/ml final concentration) of thuricin was added to 7000 μl of porcine gastric and ileum juice and incubated at 37° C. At intervals samples were taken and activity was measured with the WDA using *C. difficile* seeded plates. The samples were also assayed for the presence of the Trn-α and Trn-β peptides using MALDI-TOF MS Effect of ex vivo porcine gastric and ileal juice on the stability of the thuricin CD *C. difficile* 64539 was grown overnight and inoculated at 1.25% into Reinforced *Clostridium* Agar (RCA). Purified Thuricin CD was prepared as described above. Seven ml of porcine ileal and gastric juice was centrifuged for 15 min at 12,000 rpm to remove debris. Seventy μl (1 mg/ml) of thuricin was added to 7000 μl of porcine gastric and ileum juice and incubated at 37° C. At intervals samples were taken and activity was measured using the WDA and checked for the presence of the Trn-α and Trn-β peptides using MALDI-TOF MS.

Results

The aim of this work was to isolates narrow spectrum bacteriocin producing organisms, from within the GI tract, with high activity against *C. difficile*, which would cause the least perturbation of the resident flora of GIT.

Initial Screening for Bacteriocin Producers

From ~30,000 colonies screened from a range of faecal samples from both healthy and diseased adults, one colony was shown to produce a large zone of inhibition of the *C. difficile* overlay culture (FIG. 1). This colony was isolated from the faecal sample of a patient with IBS. Purification of this colony and growth in BHI broth showed that a potent antimicrobial compound, active against *C. difficile*, was produced into the fermentation medium; activity was lost on treatment with Proteinase K indicating that the antimicrobial substance was proteinaceous in nature (FIG. 1). This culture was stocked in the culture collection of Moorepark Food Research Centre and designated as DPC 6431; the bacteriocin was designated thuricin CD.

Identification of DPC 6431 to Species Level 16S rDNA sequencing of DPC 6431 indicated highest homology (96%) of the strain to *B. cereus/B. thuringiensis/B. anthracis*. La Duc et at (2004) have stated that *B. anthracis, B. cereus* and *B. thuringiensis* all cluster together within a very tight Glade (*B. cereus* group) phylogenetically and are thus indistinguishable from one another via 16s rDNA sequencing. DPC 6431 was subsequently identified as *B. thuringiensis* using gyrB primers. PCR products corresponding to the correct size for *B. cereus* or *B. thuringiensis* (365 and 368 respectively) were obtained with positive controls for each of these organisms. No PCR product was obtained when gyrB primers for *B. cereus* or *B. anthracis* were tested with DNA from *B. thuringiensis* DPC 6431. Due to the pathogenic nature of *B. anthracis* there was no positive control for that primer.

Characterisation of Bacteriocin from DPC 6431

Highest concentration of the thuricin CD was produced during the late log phase and stationary phase of growth probably coinciding with the onset of sporulation. Activity remained stable during the stationary phase of growth. The pH decreased during the exponential growth phase to ~5.8 from an initial pH of ~7.5; during the stationary phase the pH rose again to close to its starting value (data not shown).

The incubation of the cell free extract with 25 mg/ml of α-chymotrypsin and proteinase K resulted in complete loss of activity; incubation with pepsin or trypsin showed a 50% or 20% reduction in activity respectively after 1 h incubation at 37° C. Cell free supernatants of thuricin were active throughout the pH range 2-10 and heat stable up to 85° C., there was a reduction in activity at 90° C. and activity was lost at 100° C. after 15 minutes incubation at the respective temperatures.

Inhibition Spectrum of *B. thuringiensis* 6431

Cell free supernatant of *B. thuringiensis* 6431, when tested against a range of Gram positive and Gram negative bacteria using the WDA method, showed a narrow spectrum of inhibition inhibiting closely related *Bacillus* species such as *B. cereus*, other *B. thuringiensis* strains, *B. mycoides* and *B. firmus*; no inhibition was detected against *B. subtilis* or *B. coagulans*. Within the *Clostridium* sp. all *C. difficile* isolates tested, including *C. difficile* ribotype 027 (NCTC 13366), were very sensitive to the culture supernatants of DPC 6431 exhibiting large zones of inhibition. *C. tyrobutyricum, C. lithuseburense*, and *C. indolis* were also inhibited whereas other *Clostridium* species tested were not inhibited (*C. sporogenes*) or only weakly inhibited (*C. histolyticum* and *C. perfringens*). Among the other Gram positive pathogens tested only *Listeria monocytogenes* was sensitive to thuricin CD. Of the *lactobacillus* species tested only *L. fermentum* was strongly inhibited by thuricin CD with all other species being only very weakly inhibited (*L. crispatus* and *L. johnsonii*) or not at all. No *bifidobacteria* strains tested were sensitive to thuricin 6431. Thuricin CD showed no activity against any Gram negative organisms tested. The complete inhibition spectrum of *B. thuringiensis* 6431 is outlined in Table 1.

TABLE 1

Spectrum of inhibition of *B. thuringiensis* DPC 6431 against a range of Gram positive and Gram negative bacteria using the well diffusion assay.

| Target Strain | Strain No | Growth medium | Incubation Temperature | Sensitivity |
|---|---|---|---|---|
| *Bacillus cereus* | NCIMB 700577 | BHI[1] | 30° C. | +++ |
| *Bacillus cereus* | NCIMB 700578 | BHI | 30° C. | +++ |
| *Bacillus coagulans* | LMG 6326$^{T}$ | BHI | 30° C. | – |
| *Bacillus firmus* | LMG 7125$^{T}$ | BHI | 30° C. | ++++ |
| *Bacillus mycoides* | DPC 6335 | BHI | 30° C. | +++ |
| *Bacillus subtilis* | LMG 8198 | BHI | 30° C. | – |
| *Bacillus subtilis* | DPC 3344 | BHI | 30° C. | – |
| *Bacillus thuringiensis* | IBS 14 | BHI | 37° C. | – |
| *Bacillus thuringiensis* | LMG 7138 | BHI | 37° C. | +++ |
| *Bacteroides fragilis* | LMG 10263 | BA | 37° C. | – |
| *Bifidobacterium adolescensis* | DPC 6169 | mMRS[2] | 37° C. | – |
| *Bifidobacterium animalis* | DPC 5420 | mMRS | 37° C. | – |
| *Bifidobacterium breve* | DPC 6166 | mMRS | 37° C. | – |
| *Bifidobacterium breve* | BB12 | mMRS | 37° C. | – |
| *Bifidobacterium longum* | DSMZ 20097 | mMRS | 37° C. | – |
| *Bifidobacterium merycicum* | DSMZ 6493 | mMRS | 37° C. | – |
| *Bifidobacterium pseudolongum* | DSMZ 20092 | mMRS | 37° C. | – |
| *Campylobacter jejuni* | CI 120 | CA[3] | 37° C. | – |
| *Clostridium difficile* | ATCC 600 | RCA[4] | 37° C. | ++++ |
| *Clostridium difficile* | ATCC 43594 | RCA | 37° C. | ++++ |
| *Clostridium difficile* | R027 NCTC 13366 | RCA | 37° C. | ++++ |
| *Clostridium difficile* | 6220 | RCA | 37° C. | ++++ |
| *Clostridium difficile* | 6221 | RCA | 37° C. | ++++ |
| *Clostridium difficile* | 6219 | RCA | 37° C. | ++++ |
| *Clostridium difficile* | 6350 | RCA | 37° C. | ++++ |
| *Clostridium difficile* | 6351 | RCA | 37° C. | ++++ |
| *Clostridium difficile* | IBS 16 | RCA | 37° C. | ++++ |
| *Clostridium difficile* | Cr 15 | RCA | 37° C. | ++++ |
| *Clostridium difficile* | UC 38 | RCA | 37° C. | ++++ |
| *Clostridium difficile* | UC 38 | RCA | 37° C. | ++++ |
| *Clostridium difficile* | CR 79 | RCA | 37° C. | ++++ |
| *Clostridium difficile* | UC 47 | RCA | 37° C. | ++++ |
| *Clostridium difficile* | CR11 | RCA | 37° C. | ++++ |
| *Clostridium difficile* | UC 29 | RCA | 37° C. | ++++ |
| *Clostridium difficile* | CR 02 | RCA | 37° C. | ++++ |
| *Clostridium difficile* | UC 59 | RCA | 37° C. | ++++ |
| *Clostridium difficile* | UC 27 | RCA | 37° C. | ++++ |
| *Clostridium difficile* | H 76 | RCA | 37° C. | ++++ |
| *Clostridium difficile* | BS 47 | RCA | 37° C. | ++++ |
| *Clostridium histolyticum* | NCIMB 503 | RCA | 37° C. | + |
| *Clostridium indolis* | NCIMB 9731 | RCA | 37° C. | ++++ |
| *Clostridium lituseburense* | NCIMB 10637 | RCA | 37° C. | +++ |
| *Clostridium sporogenes* | NCIMB 9584 | RCA | 37° C. | – |
| *Clostridium tyrobutyricum* | NCIMB 8243 | RCA | 37° C. | +++ |
| *Enterobacter sakazaki* | ATCC 12869 | TSA[5] | 37° C. | – |
| *Enterobacter sakazaki* | NCTC 8155 | TSA | 37° C. | – |
| *Enterococcus casseliflavus* | LMG 10745$^{T}$ | TSA | 37° C. | – |
| *Enterococcus durans* | LMG 10746$^{T}$ | TSA | 37° C. | – |
| *Enterococcus faecalis* | LMG 7973$^{T}$ | TSA | 37° C. | – |
| *Enterococcus faecium* | LMG 7973$^{T}$ | TSA | 37° C. | – |
| *Enterococcus hirae* | LMG 6399$^{T}$ | TSA | 37° C. | – |
| *Eschericia coli* | 3786 | BHI | 37° C. | – |
| *Lactobacillus acidopuilus* | NCDO 1697 | MRS | 37° C. | – |
| *Lactobacillus bulgaricis* | LMG 6901$^{t}$ | MRS | 37° C. | – |
| *Lactobacillus casei* | ATCC 334 | MRS | 30° C. | – |
| *Lactobacillus crispatus* | LMG 9479$^{T}$ | MRS | 37° C. | + |
| *Lactobacillus curvatus* | LMG 12009 | MRS | 37° C. | – |
| *Lactobacillus fermentum* | LMG 6902 | MRS | 37° C. | +++ |
| *Lactobacillus gallinarum* | LMG 9435$^{T}$ | MRS | 37° C. | – |
| *Lactobacillus helveticus* | LH1 | MRS | 37° C. | – |
| *Lactobacillus johnsonii* | DSM 10533$^{T}$ | MRS | 37° C. | + |
| *Lactobacillus paracasei* | 338 | MRS | 37° C. | – |
| *Lactobacillus reuteri* | NCIMB 11951 | MRS | 37° C. | – |
| *Lactobacillus rhamnosus* | GG | MRS | 37° C. | – |
| *Lactobacillus ruminis* | DSM 20403$^{T}$ | MRS | 37° C. | – |
| *Lactobacillus salivarius* | UCC 118 | MRS | 37° C. | – |
| *Lactococcus lactis* | DPC 3157 | LM17 | 30° C. | + |
| *Lactococcus lactis* | HP | LM17 | 30° C. | – |
| Leuconostoc | DPC 139 | MRS | 30° C. | – |
| Leuconostoc | DPC 240 | MRS | 30° C. | – |
| *Listeria innocua* | DPC 3572 | BHI | 37° C. | +++ |
| *Listeria monocytogenes* | DPC 1768 | BHI | 37° C. | +++ |
| *Listeria monocytogenes* | DPC 3437 | BHI | 37° C. | +++ |
| *Listeria monocytogenes* | Scott A | BHI | 37° C. | +++ |

TABLE 1-continued

Spectrum of inhibition of *B. thuringiensis* DPC 6431 against a range of Gram positive and Gram negative bacteria using the well diffusion assay.

| Target Strain | Strain No | Growth medium | Incubation Temperature | Sensitivity |
|---|---|---|---|---|
| *Micrococcus luteus* | DPC 6275 | BHI | 37° C. | – |
| *Micrococcus luteus* | LMG 3293 | BHI | 30° C. | – |
| *Pediococcus pentasaceus* | LMG 11488 | MRS | 30° C. | – |
| *Propionibacterium avidium* | LMG | SLA[6] | 37° C. | – |
| *Proprionibacterium acne* | LMG | SLA | 37° C. | – |
| *Propionibacterium jensenii* | NCFB 565 | SLA | 30° C. | – |
| *Propionibacterium jensenii* | NCFB 850$^T$ | SLA | 30° C. | – |
| *Pseudomonas putida* | ATCC 33015 | BHI | 37° C. | – |
| *Pseudomonas putida* | ATCC 17522 | BHI | 37° C. | – |
| *Salmonella enterica* serovar *Typhimurium* | DPC 6046 | BHI | 37° C. | – |
| *Salmonella enterica* serovar *Derby* | DPC 6049 | BHI | 37° C. | – |
| *Staphylococcus aureus* | ATCC 25923 | TSA | 37° C. | – |
| *Staphylococcus aureus* | DPC 3767 | TSA | 37° C. | – |
| *Staphylococcus saphrophyticus* | DPC 6289 | BHI | 37° C. | – |
| *Streptococcus algalactiae* | LMG 14694$^t$ | TSA | 37° C. | – |
| *Streptococcus bovis* | DPC 5244 | BHI | 37° C. | – |
| *Streptococcus dysgalactia* | DPC 5345 | BHI | 37° C. | – |
| *Steptococcus mutans* 6159 | DPC 6159 | TSA + sucrose[7] | 37° C. | – |
| *Steptococcus mutans* 6155 | DPC 6155 | TSA + sucrose | 37° C. | – |
| *Steptococcus mutans* 6143 | DPC 6143 | TSA + sucrose | 37° C. | – |

[1]Brain heart infusion broth;
[2]Modified MRS containing 0.05% Cystein;
[3]Campylobacter agar
[4]Reinforced clostridium agar;
[5]Trypticase soya agar;
[6]Sodium lactate agar;
[7]Trypticase soya agar containing 25 mM sucrose.
(Zones of inhibition (mm) were measured and relative sensitivity determined by measuring the diameter of the zone. Zones of size ≤9 mm were designated +; of 10-15 mm were designated ++; of 16-21 mm were designated +++; of ≥22 mm were designated ++++)

Characterisation of Thuricin CD.

Figure 2:
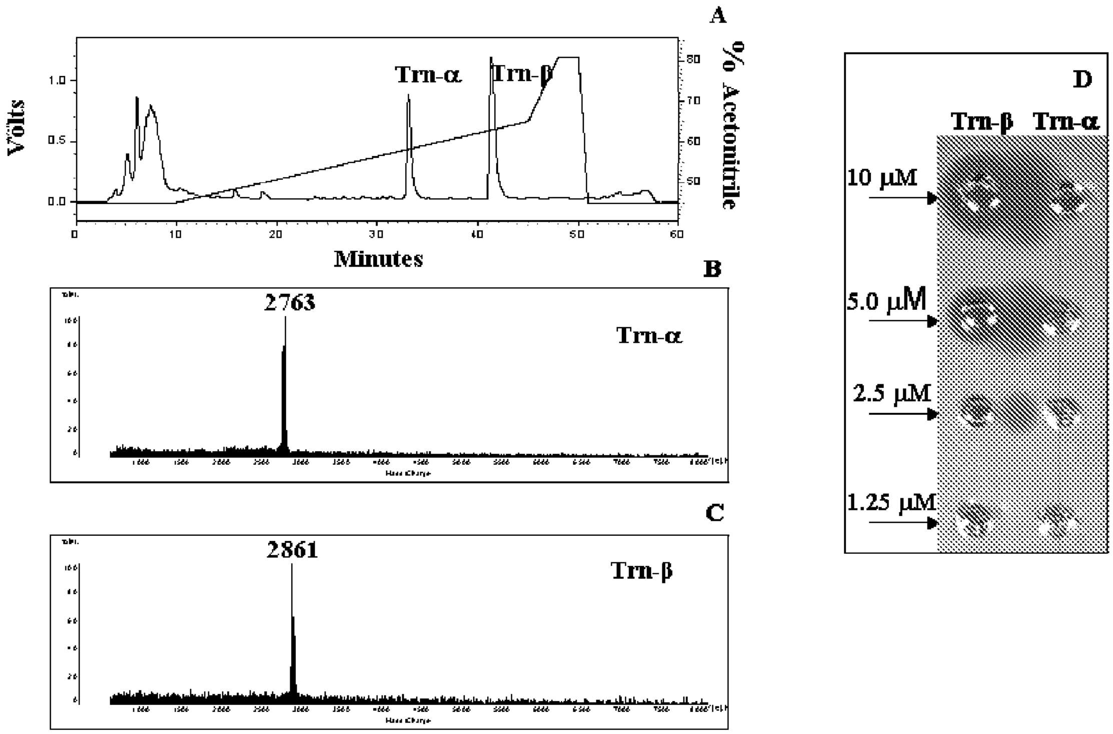
FIG. 2. RP-HPLC chromatogram of thuricin 6431 showing separation of P 1 and Trn-β (A); MALDI-TOF MS chromatograph Trn-α (B) and Trn-β (C) showing molecular mass and WDA of both peptides showing the effect of equimolar concentrations of peptides over a range of concentrations (D).
Figure 4:
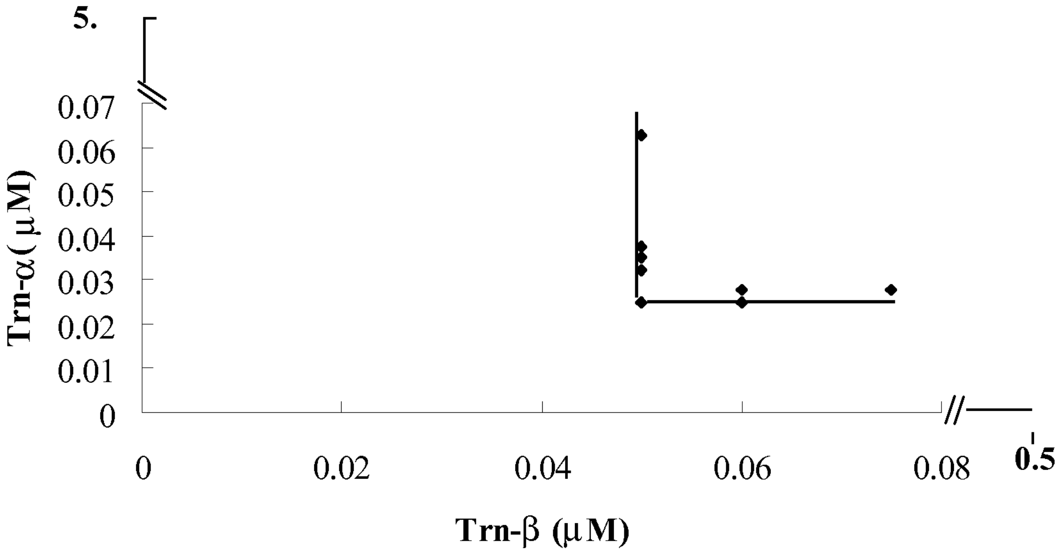
FIG. 4 Concentration of thuricin CD Trn-α and Trn-β required to inhibit growth of *C. difficile* ATCC 43493 by 50%.

Purification of thuricin using XAD beads and separation of active components using RP-HPLC resulted in 2 well-separated peaks at 26 minutes and 34 minutes (FIG. 2A) with molecular masses of 2786 and 2883 respectively. These hydrophobic peptides were designated thuricin CD Trn-α (mol mass 2883) and Trn-β (mol mass 2786) (FIGS. 2B and C). Activity was present in both the cell free supernatant and also by propan-2-ol extraction of the cell pellet indicating that thuricin is also attached to the cell wall. WDA studies of both peptides show that it is a two component bacteriocin; Trn-α has activity when present alone, however its activity is enhanced by the presence of Trn-β. At low concentrations (~2.5 μM) both peptides are required for activity using the WDA (FIG. 2D).

Elucidation of Amino Acid Sequence.

Edman degradation identified the amino acid sequence of the first 22 amino acids for thuricin CD Trn-α (G-N-A-A-C-V-[I/L]-G-C-[I/L]-G-S-C-V-[I/L]-S-E-G-[I/L]-C-N-E) and 22 amino acids for thuricin CD Trn-β (G-W-V-A-V-V-G-A-C-G-T-V-C-L-A-S-G-G-V-C-E-C-F). Despite repeated efforts it was not possible to determine further sequence data using this technique. No homologous sequences were identified when the above sequences were compared to the NCBI database.

Initial Determination of Nucleotide Sequence

The orientation of the genes encoding the two peptides is shown in FIG. 3. The PCR product obtained contains the C'-terminal end of the Trn-β peptide and the ribosomal binding site and promoter sequences for Trn-β, as well as its start codon methionine and N-terminal amino acid sequence.

Sequence Analysis of the Inverse PCR Product

The complete nucleotide sequence of the two peptides was determined together with the start codon methionine and leader peptide sequence as outlined below

```
Trn-α DNA sequence
ATGGAAGTTATGAACAATGCTTTAATTACAAAAGTAGATGAGGAGATTG

GAGGAAACGCTGCTTGTGTAATTGGTTGTAT

TGGCAGTTGCGTAATTAGTGAAGGAATTGGTTCACTTGTAGGAACAGCA

TTTACTTTAGGTTA

Trn-β DNA sequence
ATGGAAGTTTTAAACAAACAAAATGTAAATATTATTCCAGAATCTGAAG

AAGTAGGTGGTTGGGTAGCAGTAGTAGGTGC

ATGTGGTACAGTATGCTTAGCTAGTGGTGGTGTTGGAACAGAGTTTGCA

GCTGCATCTTATTTCCTATAA
```

The complete amino acid sequences of both peptides was determined and is shown below together with the leader peptide. The leader peptides are cleaved at *GG*

```
Trn-α Protein sequence
MEVMNNALITKVDEEIGGNAACVIGCIGSCVISEGIGSLVGTAFTLG

Trn-β Protein sequence
MEVLNKQNVNIIPESEEVGGWVAVVGACGTVCLASGGVGTEFAAASYFL
```

Sequence analysis of the surrounding regions reveals an upstream putative promoter located before a hypothetical protein followed by two ABC transporter systems and then the Trn-α and Trn-β peptides. Three unusual proteins are located downstream of the peptides, two radical S-adenosylmethionine SAM proteins and a C-terminal protease.

Specific Activity of Thuricin.

The isobolgram (FIG. 3) shows that the $MIC_{50}$ of thuricin Trn-β (0.5 μM) is 10 fold lower than Trn-α (5 μM) when present as individual peptides, however when the peptides are combined the $MIC_{50}$ of Trn-β is reduced to 0.05 μM when combined with 0.025 μM Trn-α indicating that thuricin Trn-α can be made 100 fold more active when low concentrations of Trn-α are added. These results show that the 2 peptides when combined at low concentrations (<1 μM) are very inhibitory to *C. difficile* when combined at a ratio of 2:1 Trn-β: Trn-α.

Figure 5:
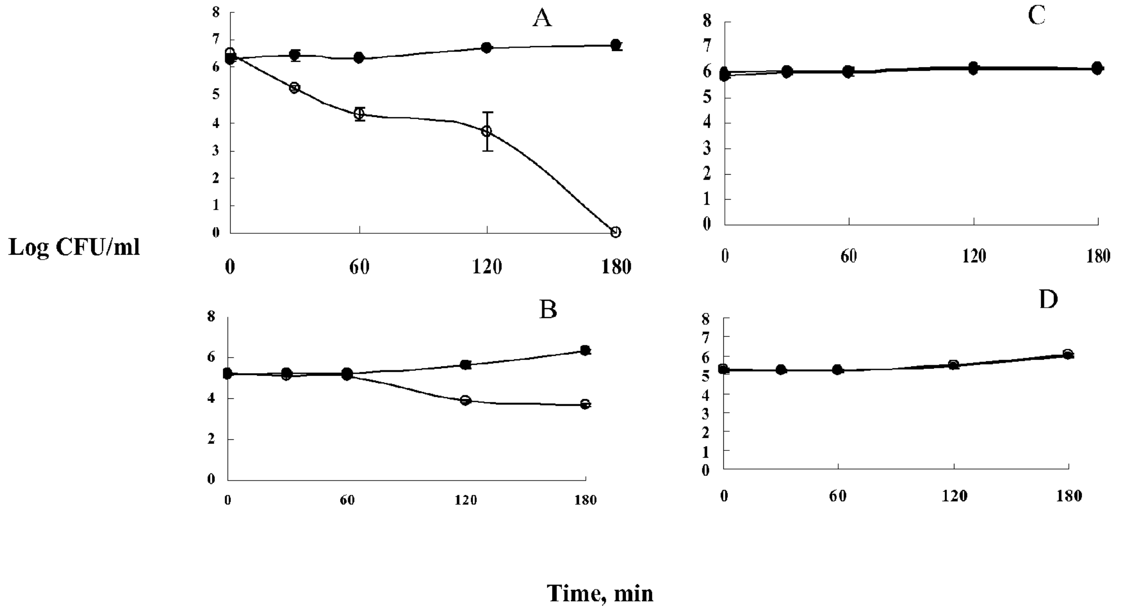
FIG. 5 The effect of Thuricin CD (200 AU/ml) on the growth of *C. difficile* R027, *L. monocytogenes, L. paracasei* 338 and *B. lactis* Bb12 at 37 C. (● Control; ○+200 AU/ml thuricin).

The bactericidal nature of thuricin CD is demonstrated in FIG. 5; initial experiments determined the concentration of thuricin required to kill *C. difficile* using kill curves. Two hundred AU thuricin/ml reduced the viable cells of *C. difficile* PCR ribotype 027 from ~$10^{6}$/ml to zero within 2 h. The same concentration of thuricin reduced the cell numbers of *L. monocytogenes* by 1.5 log cycles and had no effect on the viability of the probiotics *Lb. casei* 338 and *B. lactis* BB12 in the same time period (FIG. 5). The addition of thuricin CD to logarithmically growing *C. difficile* caused a gradual reduction of OD600 nm; this decrease in OD was paralleled with a concomitant release of the intracellular enzyme acetate kinase into the growth medium. In contrast there was no increase in the concentration of acetate kinase in the control sample without thuricin.

Thuricin CD is also effective against *C. difficile* ribotype 001 in a model faecal environment when added at 0, 8, and 16 hr (FIG. 6A). Faecal fermentations spiked with $10^6$ cfu *C. difficile* ribotype 001/ml showed that when 500 μg thuricin was added at 0, 8, and 16 hr, *C. difficile* was reduced over 1000-fold when compared with the control after 16 hr incubation. The activity of thuricin CD was mapped during the course of fermentation as demonstrated in FIG. 6B. As can be clearly seen, the addition of 500 μg of thuricin at 0, 8, and 16 hr resulted in reduction of growth of *C. difficile*. Thuricin peptides Trn-α and Trn-β were detected by RP-HPLC after 0 hr (black line) and 4 hr fermentation in the model faecal fermentation (FIG. 6C). The presence of thuricin did not affect the numbers of *Bifidobacteria* relative to control up to 16 hr incubation.

Figure 7:
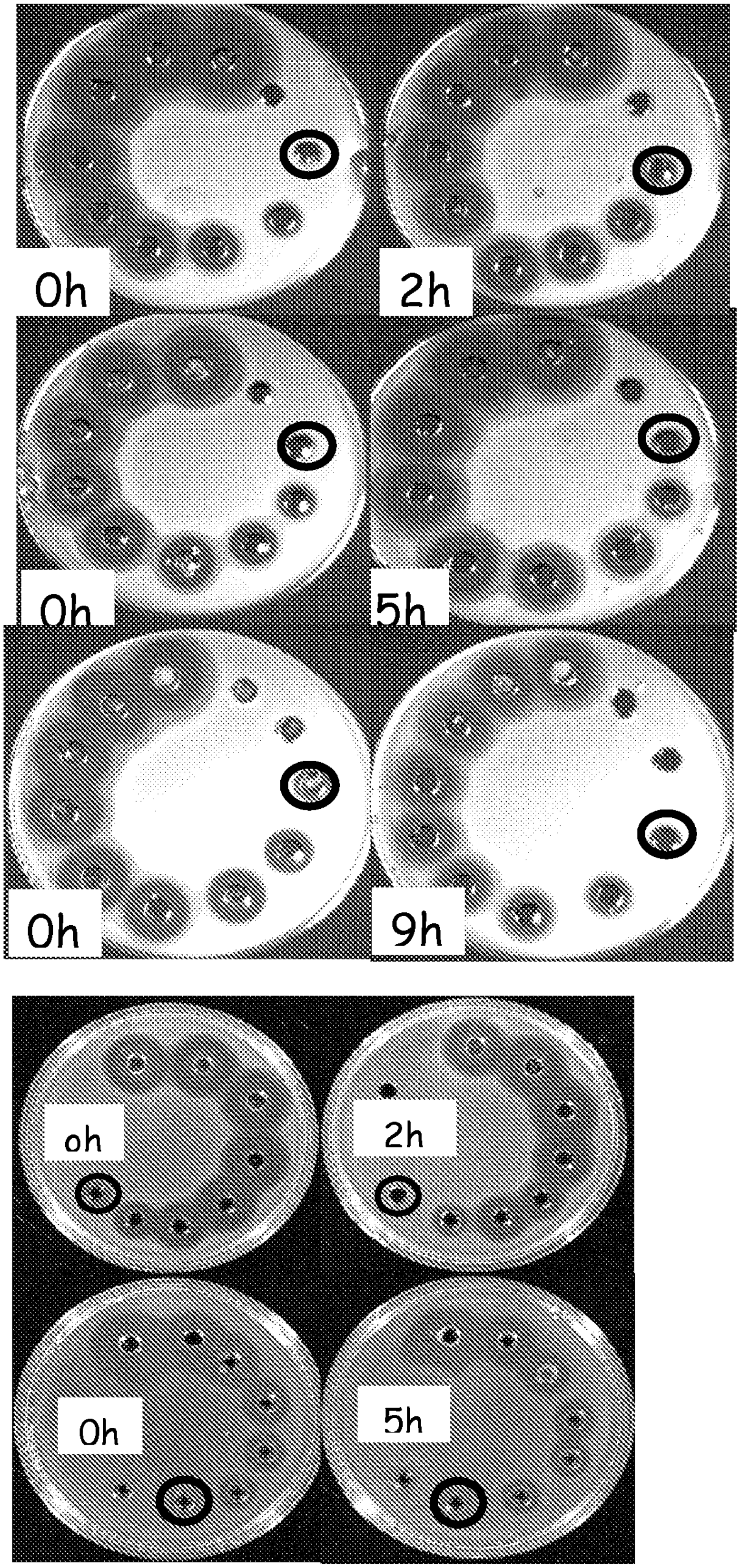
FIG. 7 Stability of thuricin CD in simulated gastric juice (A) after 2 h, simulated ileal juice (B) after 5 h, simulated colon juice (C) after 9 h, porcine gastric juice (D) after 2 h and porcine ileal juice (E) after 5 h incubation at 37° C.

Studies on the stability of the thuricin peptides Trn-α and Trn-β in simulated gastric (FIG. 7A), ileal (FIG. 7B) and colon juice (FIG. 7C) demonstrated that there was no reduction of activity in any of the simulated gut environments when thuricin CD was incubated for 2, 4, or 9 hours in gastric, ileal and colon juice, respectively. Furthermore, incubation of thuricin peptides Trn-α and Trn-β for 2 hr and 5 hr in ex vivo procine gastric juice (FIG. 7D) and ileal juice (FIG. 7E), respectively, also demonstrated no reduction in activity. The results for determining the minimum inhibitory concentration of thuricin shows that clinically significant ribotypes of *C. difficile* are more sensitive to thuricin when compared to the antibiotics vancomycin and metronidazole, which are currently used for treatment, as shown in the Table 2 below. Ribotype 001 and 106 are commonly associated with outbreaks of CDAD in Irish and UK hospitals respectively, while ribotype 027 is associated with increased severity of symptoms and increased morbidity due to the elevated toxin production resulting in disease that is more refractory to treatment.

TABLE 2

Comparison of minimum inhibitory concentrations (MIC) for thuricin, vancomycin and metronidazole against a range of clinically significant ribotypes of *C. difficile.*

| *C. difficile* | MIC (μM) | | |
|---|---|---|---|
| Ribotype | Thuricin | Vancomycin | Metronidazole |
| 001 | 0.097 | 0.39 | 3.125 |
| 106 | 0.125 | 0.39 | 1.56 |
| 027 | 0.012 | 0.39 | 3.125 |

Discussion

Due to the high incidence of *C. difficile* worldwide in hospitals and facilities for the elderly radical approaches have to be considered for the treatment of this disease. The two component lantibiotic lacticin 3147 has been shown to be very effective in killing *C. difficile* at low concentrations, however, as it is a broad spectrum antibiotic it also affected the *Lactobacillus* and *Bifidobacterium* populations (by 3 log cycles) in simple faecal fermentations at concentrations required to kill *C. difficile* (Rea et al., 2007).

The work reported here focused on searching within the GI tract for sources of antimicrobial producing bacteria to address this problem. The aim was to isolate a narrow spectrum bacteriocin producer, which would have potent activity against *C. difficile* while perturbing the gut microbiota as little as possible. As a result of screening ~30,000 colonies from faecal samples one colony was detected that showed inhibition of the *C. difficile* overlay. The faecal samples had been pre-treated with ethanol to facilitate the isolation of spore forming bacteria. The fact that just one antimicrobial producing colony was isolated from just one sample at a low dilution would suggest that the *B. thuringiensis* strain DPC 6431 isolated was not a major constituent of the gut microbiota.

Characterisation of the antimicrobial peptide produced by DPC 6431, thuricin CD, demonstrated that its antimicrobial inhibition spectrum (using WDA) is narrow and while very effective against *C. difficile* isolates including the PCR ribotype 027 has little or no activity against the beneficial microflora such as the *Lactobacillus* and *Bifidobacterium* populations.

*B. thuringiensis* is a spore forming Gram positive insect pathogen which has been used extensively for many years in biological pest control. Bacteriocins have been identified previously from a number of *B. thuringiensis* strains (Ahern et al., 2003; Barboza-Corona et al., 2007; Chechimi et al. 2007; Cherif et al., 2003; Cherif et al., 2001; Favret & Yousten, 1989; Gray et al., 2006a; Gray et al. 2006b; Kamoun et al., 2005). Ahern et at 2003 characterised a BUS substance from a strain of *B. thuringiensis* which produced 2 active peptides designated thuricin 439a and thuricin 439b; both peptides showed antimicrobial activity however two component activity was not reported. From a survey of the literature the sequence and molecular mass of thuricin 6431 is most similar to that produced by *B. thuringiensis* 439. Ahern et at (2003) reported that the amino acid sequences of the two peptides 439a and 439b were identical but the peptides have different molecular weights. The sequence reported for thuricin 439a/b has 2 unidentified amino acids (x) which the authors suggest are likely to be cystein, therefore, there is just 2 amino acid distinguishing (a cystein instead of a valine and a glutamic acid instead of valine) in the first 19 amino acids of the peptides from *B. thuringiensis* 6431 and 439. However, Trn-α from thuricin CD is significantly different from thuricin 439 peptide. Thuricin CD was shown to be very active against a range of *Clostridium* species while no anti-clostridium activity was reported for thuricin 439 (Ahern et al., 2003). A comparison between the amino acid sequences and molecular masses and spectrum of activity of Thuricin CD and 439 is shown below in Table 3.

TABLE 3

Comparison of thuricin identified in this study with thuricin 439 of Aherne et at (2003)

| Bacteriocin | Amino Acid Sequence | Mol Mass (Da) | Inhibitory activity against *Clostridium* species |
|---|---|---|---|
| Thuricin CD Trn-α | G-N-A-A-C-V-I-G-C-I-G-S-C-V-I-S-E-G-I-G-SLVGTAFTLG | 2763 | Yes |
| Thuricin CD Trn-β | G-W-V-A-V-V-G-A-C-G-T-V-C-L-A-S-G-G-V-G-T-E-F-A-A-A-S-Y-F-L | 2861 | Yes |
| Thuricin 439 a | G-W-V-A-X-V-G-A-X-G-T-V-V-L-A-S-G-G-V-V | 2919.9 | No |
| Thuricin 439 b | G-W-V-A-X-V-G-A-X-G-T-V-V-L-A-S-G-G-V-V | 2803.8 | No |

The nucleic acid sequence and the orientation of the genes encoding the thuricin peptides peptide 1 and peptide 2 are shown in FIG. 3. A search of the NCBI database showed no homologous sequences to the sequences identified here. The discrepancies between the mol masses as determined by MALDI-TOF MS (2763 and 2861) and from the amino acid sequence (2770 and 2864) of thuricin CD would appear to be the result of post translational modification. The predicted mass from the DNA sequence of Trn-α and Trn-β peptides, 2769 Da and 2876 Da, respectively, differ by 6 mass units from what was obtained from MS (mass spectrometry). For Trn-α, the differences in mass indicate a loss of two hydrogen atoms from each of Ser 21, Thr 25, and Thr 28, and for Trn-β is suggestive that Thr 21, Ala 25, and Tyr 28 are all two mass units lighter than expected. Cys residues for both peptides are in the same positions (residues 5, 9, and 13), while the post-translational modifications occur at the same positions (residues 21, 25, and 28)

Thuricin CD is active over a wide pH range and moderately heat stable retaining activity up to 95° C. for 15 minutes. $MIC_{50}$ studies show it to be a very potent inhibitor of *C. difficile* at concentrations as low as 0.5 and 5 μM (Trn-α and Trn-β respectively) when present as single peptides but the $MIC_{50}$ is reduced to 0.05 μM when both peptides are present indicating that thuricin is a 2 component bacteriocin highly active against *C. difficile* at low concentrations. Kill curves demonstrated that thuricin CD is very effective in reducing cell numbers of *C. difficile* ribotype 027 (NAP 1) at low concentrations and is also lytic in nature. The efficacy of thuricin against *C. difficile* 027 is significant as this strain has been shown to be hyper virulent, the incidence of which is increasing worldwide resulting in increased severity, high relapse rate and significant mortality (Kuiper et al 2007). Comparisons of MIC values for thuricin with those obtained for vancomycin and metronidazole, which are the current antibiotics used to treat *C. difficile* infections are clinically significant. Interestingly, similar concentration of thuricin CD did not affect the viability of *L. casei* 338 or *B. lactis* Bb 12 in contrast to the effect of lacticin (Rea et at 2007) which would indicate that beneficial flora in the gut would not be perturbed by this antimicrobial. When assessing microbially derived peptides for the treatment or prevention of disease the issue of bio-availability needs to be addressed. The demonstrated degradation of the antimicrobial activity of thuricin CD in vitro with α-chymotrypsin and pepsin and trypsin would suggest that this bacteriocin would not survive gastric transit without protection such as encapsulation. However, the alternative strategy of feeding spores or vegetative cells of this organism as probiotics could be investigated as a method to target the delivery of this peptide within the GIT. Probiotic cultures are usually associated with species of bacteria which are normal inhabitants of the GIT such as *Lactobacillus* and *Bifidobacterium* species. However, *S. boulardii* which is not a normal constituent of the human gut microbiota is currently used as a probiotic in the treatment of CDAD. *Bacillus* species are currently being used as probiotic cultures for both human and animal use (for reviews see Hong et al 2005 and Sanders et al 2003). Because spores can survive hostile environments the question has been raised as to their true habitat? While it would have been assumed that they arrive in the human gut as a consequence of ingestion of the spore from the environment, Hong et al (2005) state however, that there is the possibility that *Bacillus* species exist in an endosymbiotic relationship with their host being able temporarily to survive and proliferate in the gut. The advantage of administering spores over vegetative cells is their stability and ability to pass through the hostile environment of the stomach. In mouse studies it has been shown that while vegetative cells of *B. subtilus* did not survive passage through the stomach almost all of the administered spores survived gastric transit and were recovered in the small intestine (Duc et al 2003).

In a study of greenhouse workers excreting *B. thuringiensis* due to occupational exposure to *B. thuringiensis*-based pesticides no gastrointestinal symptoms correlated with the presence of *B. thuringiensis* in the faecal samples (Jensen et al 2002). A study of *B. thuringiensis* in the gut of human-flora-associated rats which had been fed *B. thuringiensis* spores and vegetative cells detected no adverse effects on the composition of the indigenous gut flora or no cytotoxic effect in gut samples by Vero cell assay (Wilcks et al., 2006).

Although there is a discrepancy between the results using the purified proteolytic enzymes and the result in the various GI environments, an explanation for this may be that the concentration of the purified enzymes used is much greater than that present in the GI environments. Note that these results refer to the thuricin peptides only and not the vegetative cells or spores.

In conclusion this work has shown that the *B. thuringiensis* strain DPC 6431 produces a potent heat stable two-component bacteriocin which has potential as a novel therapeutic agent CDAD either in peptide form or as a probiotic in either a vegetative cell or spore format.

The bacteriocin of the invention has a number of advantages. The antimicrobial substance designated thuricin CD was produced into the fermentation medium (1 liter of medium yielded 350 mg thuricin) and the cell free supernatant showed a narrow spectrum of inhibition inhibiting *Bacillus* species, *C. difficile* including PCR ribotype 027, *C. perfringens* and *Listeria monocytogenes. Bifidobacterium* and *Lactobacillus* species were not inhibited with the exception of *Lb. fermentum* and *Lb. crispatus* and *Lb. johnsonii*, which were very weakly inhibited. The bacteriocin is heat stable, active over a wide pH range and is sensitive to a range of proteolytic enzymes. It is a two-component bacteriocin with the peptides having molecular masses of 2763 (Trn-α) and 2861 (Trn-β). Thuricin CD exhibited an $MIC_{50}$ of 0.5 μM and 5 μM for Trn-β and Trn-α respectively, when both peptides were present alone. When the peptides were present together the $MIC_{50}$ was 50 nM Trn-β in combination with 25 nM of Trn-α; a ratio of 2:1. The bactericidal effect of thuricin CD was demonstrated through time kill experiments in which ~$5\times10^6$ cfu of *C. difficile* per ml were killed within 180 min at concentration of 200 AU/ml. Thuricin CD is a two component bacteriocin active at nano molar concentrations.

REFERENCES

Ahern, M., Verschueren, S. & van Sinderen, D. (2003). Isolation and characterisation of a novel bacteriocin produced by *Bacillus thuringiensis* strain B439. *FEMS Microbiology Letters* 220, 127-131.

Aronsson, B., Mollby, R. & Nord, C. E. (1985). Antimicrobial agents and *Clostridium difficile* in acute enteric disease: epidemiological data from Sweden, 1980-1982. *The Journal of Infectious Diseases* 151, 476-481.

Barboza-Corona, J. E., Vazquez-Acosta, H., Bideshi, D. K. & Salcedo-Hernandez, R. (2007). Bacteriocin-like inhibitor substances produced by Mexican strains of *Bacillus thuringiensis. Archives of Microbiology* 187, 117-126.

Bartlett, J. G. (2006). Narrative review: The New Epidemic of *Clostridium difficile*-Associated Enteric Disease. *Annals of Internal Medicine* 145, 758-764.

Bartoloni, A., Mantella, A., Goldstein, B. P., Dei, R., Benedetti, M., Sbaragli, S. & Paradisi, F. (2004). In-vitro activity of nisin against clinical isolates of *Clostridium difficile. Journal of Chemotherapy* 16, 119-121.

Beumer, R. R., J. de Vries, and F. M. Rombouts. (1992). *Campylobacter jejuni* non-culturable coccoid cells. In. J. Food Microbiol. 15 153-263.

Bizani, D., Dominguez, A. P. & Brandelli, A. (2005). Purification and partial chemical characterization of the antimicrobial peptide cerein 8A. *Letters in Applied Microbiology* 41, 269-273.

Chechimi, S., Delalande, F., Sablé S, Hajlaoui M R, Van Dorsselaer A, Limam F, and Pons A M. (2007). Purification and partial amino acid sequence of thuricin S, a new anti-*Listeria* bacteriocin from *Bacillus thuringiensis. Can. J. Microbiol.* 53(2): 284-290.

Cherif, A., Chehimi, S., Limem, F., Hansen, B. M., Hendriksen, N. B., Daffonchio, D. & Boudabous, A. (2003). Detection and characterization of the novel bacteriocin entomocin 9, and safety evaluation of its producer, *Bacillus thuringiensis* ssp. entomocidus HD9. *Journal of Applied Microbiology* 95, 990-1000.

Cherif, A., Ouzari, H., Daffonchio, D., Cherif, H., Ben Slama, K., Hassen, A., Jaoua, S. & Boudabous, A. (2001). Thuricin 7: a novel bacteriocin produced by *Bacillus thuringiensis* BMG1.7, a new strain isolated from soil. *Letters in Applied Microbiology* 32, 243-247.

Favret, M. E. & Yousten, A. A. (1989). Thuricin: the bacteriocin produced by *Bacillus thuringiensis. Journal of Invertebrate Pathology* 53, 206-216.

Fooks, L. J., and G. R. Gibson (2003). Mixed culture fermentation studies on the effects of synbiotics on the human intestinal pathogens *Campylobacter jejuni* and *Escherichia coli*. Anaerobe 9 231-242.

George, R. H., Symonds, J. M., Dimock, F., Brown, J. D., Arabi, Y., Shinagawa, N., Keighley, M. R., Alexander-Williams, J. & Burdon, D. W. (1978). Identification of *Clostridium difficile* as a cause of pseudomembranous colitis. *British Medical Journal* 1, 695.

Gray, E. J., Lee, K. D., Souleimanov, A. M., Di Falco, M. R., Zhou, X., Ly, A., Charles, T. C., Driscoll, B. T. & Smith, D. L. (2006a). A novel bacteriocin, thuricin 17, produced by plant growth promoting rhizobacteria strain *Bacillus thuringiensis* NEB17: isolation and classification. *Journal of Applied Microbiology* 100, 545-554.

Gray, E. J., Di Falco, M., Souleimanov, A. M., and Smith, D. L. (2006b). Proteomic analysis of the bacteriocin thuricin 17 produced by *Bacillus thuingiensis* NEB17. *FEMS Microbiol. Lett.* 255(1): 27-32.

Hall, I. C. & O'Toole, E. (1935). Intestinal flora in new-born infants with a description of a new pathogenic anaerobe, *Bacillus difficilis. Amer Journal of Diseases in Childhood* 49, 390-402.

Kamoun, F., Mejdoub, H., Aouissaoui, H., Reinbolt, J., Hammami, A. & Jaoua, S. (2005). Purification, amino acid sequence and characterization of Bacthuricin F4, a new bacteriocin produced by *Bacillus thuringiensis. Journal of Applied Microbiology* 98, 881-888.

Kemperman, R., Kuipers, A., Karsens, H., Nauta, A., Kuipers, O. & Kok, J. (2003). Identification and characterization of two novel clostridial bacteriocins, circularin A and closticin 574. *Applied and Environmental Microbiology* 69, 1589-1597.

Padilla, C., Lobos, O., Brevis, P., Abaca, P. & Hubert, E. (2006). Plasmid-mediated bacteriocin production by *Shigella flexneri* isolated from dysenteric diarrhoea and their transformation into *Escherichia coli. Letters in Applied Microbiology* 42, 300-303.

Rea, M. C., Clayton, E., O'Connor, P., Shanahan, F., Kiely, B., Hill, C. & Ross, R. P. (2007). Antomicrobial activity of lacticin 3147 against clinical *Clostridium difficile* strains. *Journal of Medical Microbiology* 56, In press.

Rogers, L. A. & Whittier, E. O. (1928). Limiting Factors in the Lactic Fermentation. *Journal of Bacteriology* 16, 211-229.

Ryan, M. P., Rea, M. C., Hill, C. & Ross, R. P. (1996). An application in cheddar cheese manufacture for a strain of *Lactococcus lactis* producing a novel broad-spectrum bacteriocin, lacticin 3147. *App. and Environmental Microbiol.* 62, 612-619.

Sebei S, Zendo T, Boudabous A, Nakayama J, Sonomoto K. (2007). Characterization, N-terminal sequencing and classification of cerein MRX1, a novel bacteriocin purified from a newly isolated bacterium: *Bacillus cereus* MRX1. *J Appl Microbiol.* 103(5):1621-31.

Simpson, P. J., Stanton, C., Fitzgerald, G. F. & Ross, R. P. (2003). Genomic diversity and relatedness of *bifidobacteria* isolated from a porcine cecum. *Journal of Bacteriology* 185, 2571-2581.

Teo, A. Y. & Tan, H. M. (2005). Inhibition of *Clostridium perfringens* by a novel strain of *Bacillus subtilis* isolated from the gastrointestinal tracts of healthy chickens. *Applied and Environmental Microbiology* 71, 4185-4190.

Trautner, B. W., Hull, R. A. & Darouiche, R. O. (2005). Colicins prevent colonization of urinary catheters. *The Journal of Antimicrobial Chemotherapy* 56, 413-415.

Wilcks, A., Hansen, B. M., Hendriksen, N. B. & Licht, T. R. (2006). Persistence of *Bacillus thuringiensis* bioinsecticides in the gut of human-flora-associated rats. *FEMS Immunology and Medical Microbiology* 48, 410-418.

Winstrom, J., Norrby, S. R., Myhre, E. B., Eriksson, S., Granstrom, G., Lagergren, L. & al, e. (2001). Frequency of antibiotic-associated diarrhoea in 2462 antibiotic-treated hospitalised patients: a prospective study. *J. of Antimicrobial Chemotherapy* 47, 43-50.

Yamada, S., Ohashi, E., Agata, N. & Venkateswaran, K. (1999). Cloning and nucleotide sequence analysis of gyrB of *Bacillus cereus, B. thuringiensis, B. mycoides*, and *B. anthracis* and their application to the detection of *B. cereus* in rice. *Applied and Environmental Microbiology* 65, 1483-1490.

Yudina T. G., Brioukhanov, A. L., Zalunin, I. A., Revina, L. P., Shestakoc, A. I., Voyushina, N. E., Chestukhina, G. G., and Netrusov, A. I. (2007). Antimicrobial activity of different proteins and their fragments from *Bacillus thuringiensis* parasporal cystals against clostridia and archaea. *Anaerobe* 13, 6-13.

The invention claimed is:

1. A biologically pure *Bacillus thuringiensis* strain 6431 as deposited with the National Collection of Industrial and Marine Bacteria under the Accession No. 41490 encoding a bacteriocin effective against *Clostridium difficile* and *Listeria monocytogenes*.

2. A disinfectant composition comprising the biologically pure bacterial strain of claim 1.

3. A sporicidal composition comprising the biologically pure bacterial strain of claim 1.

4. A pharmaceutical composition comprising the biologically pure bacterial strain of claim 1 and a pharmaceutically acceptable carrier.

5. The pharmaceutical composition as claimed in claim 4 formulated as an enema preparation.

6. The pharmaceutical composition as claimed in claim 4 containing encapsulated peptides adapted for targeting the colon.

7. A Topical composition comprising the biologically pure bacterial strain of claim 1 and a carrier, for the treatment of wounds and skin infections for gas gangrene caused by *Clostridium* spp.

8. A bacteriocin designated Thuricin CD effective against *Listeria monocytogenes* and *Clostridium difficile*, produced by a bacterial strain *Bacillus thuringiensis* strain 6431 as deposited with the National Collection of Industrial and Marine Bacteria under the Accession No. 41490 wherein the Thuricin CD comprises 2 peptides, Trn-α and Trn-β, the Trn-α having a molecular mass of about 2763 daltons and the Trn-β having a molecular mass of about 2861 daltons.

9. The bacteriocin as claimed in claim 8 being heat-stable up to about 85° Centigrade.

10. The bacteriocin as claimed in claim 8 having a reduction of activity at about 90° Centigrade and a loss of activity at about 100° Centigrade after 15 minutes of incubation.

11. The bacteriocin as claimed in claim 8 having the ability to further inhibit *Bacillus cereus, Bacillus thuringiensis* strains IBS 14 and LMG 7138, *Bacillus mycoides, Bacillus firmus, Clostridium difficile* ribotype 027, *Clostridium tyrobutyricum, Clostridium lithuseburense, Clostridium indolis* and *Clostridium perfringens*.

12. The bacteriocin as claimed in claim 8 being active in the pH range 2-10.

13. The bacteriocin as claimed in claim 8 having a bacteriocidal effect against *Clostridium difficile* of approximately $5\times10^6$CFU of *Clostridium difficile* per ml being killed within 180 minutes when Thuricin CD is present at a concentration of 200 AU/ml.

14. The bacteriocin as claimed in claim 8 having a minimum inhibitory concentration of 0.097 μM, 0.125 μM and 0.012 μM against *Clostridium difficile* Ribotype 001, 106 and 027, respectively.

15. The bacteriocin as claimed in claim 8 in which the Trn-α has an amino acid sequence consisting of GNAACVIGCIGSCVISEGIGSLVGTAFTLG and the Trn-β has an amino acid sequence consisting of GWVAVVGACGTVCLASGGVGTEFAAASYFL.

* * * * *

SEQUENCE LISTING

```
<160> NUMBER OF SEQ ID NOS: 13

<210> SEQ ID NO 1
<211> LENGTH: 30
<212> TYPE: PRT
<213> ORGANISM: Bacillus thuringiensis

<400> SEQUENCE: 1

Gly Asn Ala Ala Cys Val Ile Gly Cys Ile Gly Ser Cys Val Ile Ser
1               5                   10                  15

Glu Gly Ile Gly Ser Leu Val Gly Thr Ala Phe Thr Leu Gly
            20                  25                  30


<210> SEQ ID NO 2
<211> LENGTH: 30
<212> TYPE: PRT
<213> ORGANISM: Bacillus thuringiensis

<400> SEQUENCE: 2

Gly Trp Val Ala Val Val Gly Ala Cys Gly Thr Val Cys Leu Ala Ser
1               5                   10                  15

Gly Gly Val Gly Thr Glu Phe Ala Ala Ala Ser Tyr Phe Leu
            20                  25                  30


<210> SEQ ID NO 3
<211> LENGTH: 44
<212> TYPE: DNA
<213> ORGANISM: Artificial
<220> FEATURE:
<223> OTHER INFORMATION: Synthetic Primer

<400> SEQUENCE: 3

ggttgggtag cagtagtagg tgcatgtggw acagtwaccc awcc                      44


<210> SEQ ID NO 4
<211> LENGTH: 44
<212> TYPE: DNA
<213> ORGANISM: Artificial
<220> FEATURE:
<223> OTHER INFORMATION: Synthetic Primer

<400> SEQUENCE: 4

cgtaaacata ctgtaccaca tgcacctact acwgcwaccc awcc                      44


<210> SEQ ID NO 5
<211> LENGTH: 29
<212> TYPE: DNA
<213> ORGANISM: Artificial
<220> FEATURE:
<223> OTHER INFORMATION: Synthetic Primer
```

<400> SEQUENCE: 5
ggtaatgcat gtgtawtwgg wtgtwtwgg 29

<210> SEQ ID NO 6
<211> LENGTH: 32
<212> TYPE: DNA
<213> ORGANISM: Artificial
<220> FEATURE:
<223> OTHER INFORMATION: Synthetic Primer

<400> SEQUENCE: 6
ccaatacgac caattacaca wgcwgcwttw cc 32

<210> SEQ ID NO 7
<211> LENGTH: 23
<212> TYPE: DNA
<213> ORGANISM: Artificial
<220> FEATURE:
<223> OTHER INFORMATION: Synthetic Primer

<400> SEQUENCE: 7
catgcaccta ctgctaccca acc 23

<210> SEQ ID NO 8
<211> LENGTH: 27
<212> TYPE: DNA
<213> ORGANISM: Artificial
<220> FEATURE:
<223> OTHER INFORMATION: Synthetic Primer

<400> SEQUENCE: 8
cagagtttgc agctgcatct tatttcc 27

<210> SEQ ID NO 9
<211> LENGTH: 47
<212> TYPE: PRT
<213> ORGANISM: Bacillus thuringiensis

<400> SEQUENCE: 9

```
Met Glu Val Met Asn Asn Ala Leu Ile Thr Lys Val Asp Glu Glu Ile
1               5                   10                  15

Gly Gly Asn Ala Ala Cys Val Ile Gly Cys Ile Gly Ser Cys Val Ile
            20                  25                  30

Ser Glu Gly Ile Gly Ser Leu Val Gly Thr Ala Phe Thr Leu Gly
        35                  40                  45
```

<210> SEQ ID NO 10
<211> LENGTH: 49
<212> TYPE: PRT
<213> ORGANISM: Bacillus thuringiensis

<400> SEQUENCE: 10

```
Met Glu Val Leu Asn Lys Gln Asn Val Asn Ile Ile Pro Glu Ser Glu
1               5                   10                  15

Glu Val Gly Gly Trp Val Ala Val Val Gly Ala Cys Gly Thr Val Cys
            20                  25                  30

Leu Ala Ser Gly Gly Val Gly Thr Glu Phe Ala Ala Ala Ser Tyr Phe
        35                  40                  45

Leu
```

<210> SEQ ID NO 11

-continued

```
<211> LENGTH: 143
<212> TYPE: DNA
<213> ORGANISM: Bacillus thuringiensis

<400> SEQUENCE: 11

atggaagtta tgaacaatgc tttaattaca aaagtagatg aggagattgg aggaaacgct     60

gcttgtgtaa ttggttgtat tggcagttgc gtaattagtg aaggaattgg ttcacttgta    120

ggaacagcat ttactttagg tta                                           143


<210> SEQ ID NO 12
<211> LENGTH: 150
<212> TYPE: DNA
<213> ORGANISM: Bacillus thuringiensis

<400> SEQUENCE: 12

atggaagttt taaacaaaca aaatgtaaat attattccag aatctgaaga agtaggtggt     60

tgggtagcag tagtaggtgc atgtggtaca gtatgcttag ctagtggtgg tgttggaaca    120

gagtttgcag ctgcatctta tttcctataa                                    150


<210> SEQ ID NO 13
<211> LENGTH: 490
<212> TYPE: DNA
<213> ORGANISM: Bacillus thuringiensis

<400> SEQUENCE: 13

attgtacttt ctattacgta tttatattcc attaaggaat ttaaattcaa taaatttgct     60

taaaacattt tgaagaagag gatcttaaaa ataaggagga attaatcatg gaagttttaa    120

acaaacaaaa tgtaaatatt attccagaat ctgaagaagt aggtggttgg gtagcagtag    180

taggtgcatg tggtacagta tgcttagcta gtggtggtgt tggaacagag tttgcagctg    240

catcttattt cctataagaa ttaagtaaac ataaaatgat taaaaaaata aggaggaatt    300

aatcatggaa gttatgaaca atgctttaat tacaaaagta gatgaggaga ttggaggaaa    360

cgctgcttgt gtaattggtt gtattggcag ttgcgtaatt agtgaaggaa ttggttcact    420

tgtaggaaca gcatttactt taggttaaaa atatatattt acacagaata gcacaaaaac    480

atttagtaaa                                                          490
```